United States Patent [19]

Moeller et al.

[11] Patent Number: 4,939,171

[45] Date of Patent: Jul. 3, 1990

[54] SEBOSUPPRESSIVE TOPICAL PREPARATIONS

[75] Inventors: Hinrich Moeller, Monheim; Norbert Banduhn, Erkrath, both of Fed. Rep. of Germany

[73] Assignee: Henkel Kommanditgesellschaft auf Aktien, Duesseldorf, Fed. Rep. of Germany

[21] Appl. No.: 269,941

[22] Filed: Nov. 10, 1988

[30] Foreign Application Priority Data

Nov. 12, 1987 [DE] Fed. Rep. of Germany ....... 3738406

[51] Int. Cl.$^5$ .................. A61K 31/215; A61K 31/19; A61K 31/045
[52] U.S. Cl. .................................. 514/530; 514/543; 514/544; 514/568; 514/570; 514/571; 514/729
[58] Field of Search ............... 514/530, 570, 571, 543, 514/544, 568, 729

[56] References Cited

U.S. PATENT DOCUMENTS 4,503,244  3/1985  Moeller et al. ..................... 514/544

Primary Examiner—Leonard Schenkman
Attorney, Agent, or Firm—Ernest G. Szoke; Wayne C. Jaeschke; Norvell E. Wisdom, Jr.

[57] ABSTRACT

Alkyl and alkenyl aryl ether derivatives corresponding to the formula:

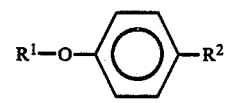

(I)

in which $R^1$ is a saturated cycloaliphatic $C_6$–$C_{20}$ alkyl group or a mono- or polyunsaturated, linear, branched or cycloaliphatic $C_6$–$C_{20}$ alkyl group and $R^2$ is a $C_1$–$C_4$ hydroxyalkyl group, a $C_3$ or $C_4$ hydroxyalkenyl group, a group —COOR$^3$, —CH$_2$—COOR$^3$, —CH$_2$—CH$_2$—COOR$^3$ or —CH=CH—COOR$^3$, are suitable as sebosuppressive agents in cosmetic or pharmaceutical preparations for topical application to the hair and to the skin.

16 Claims, No Drawings

SEBOSUPPRESSIVE TOPICAL PREPARATIONS

Field of the Invention

This invention relates to the use of alkyl and alkenyl aryl ether derivatives having a special structure as antiseborrhoeic agents in topical pharmaceutical or cosmetic sebosuppressive preparations.

Description of Related Art

Excessive secretions of the sebaceous glands of the epidermis can lead to skin disorders. In milder cases which occur fairly frequently, excessive secretions cause a greasy appearance of the hair or a shiny, oily appearance of the skin. Accordingly, efforts are being made in modern cosmetics to normalize the secretion of the sebaceous glands by suitable topical preparations and to restore the hair and the skin to an attractive appearance. Furthermore, in severe cases, seborrhoea can become a medical problem, for which appropriate therapy is needed.

Antiseborrhoeic additives which have already been proposed for cosmetic preparations include 4-alkoxybenzyl alcohols and phenetols (German patent application DE-A 33 32 505), 4-alkoxybenzoic acid esters (German patent application DE-A 31 21 064, DE-A 35 00 971 and European patent application EP-A 114 051), 4-alkoxybenzoic acids and salts thereof (German patent applications DE-A 30 47 106 and DE-A 35 00 972), alkoxycinnamic acid esters (German patent application DE-A 31 21 091) and $C_1$-$C_6$ alkoxyphenylpropionic acid esters (German patent application DE-A 30 47 106).

Although the compounds taught in the cited references show a distinct antiseborrhoeic effect, there is still a need for improved preparations having good antiseborrhoeic activity at low concentrations.

Description of the Invention

Except in the operating examples, all numbers herein describing compositions or reaction conditions are to be understood as modified by the term "about".

Compounds have now been found which show good antiseborrhoeic activity at concentrations of only 0.001% by weight and lower in vehicles suitable for topical application. These compounds are alkyl and alkenyl aryl ether derivatives corresponding to the formula:

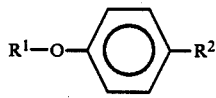 (I)

in which $R^1$ is a saturated, cycloaliphatic $C_6$-$C_{20}$ alkyl group or a mono- or polyunsaturated, linear, branched or cycloaliphatic $C_6$-$C_{20}$ alkyl group and $R^2$ is a $C_1$-$C_4$ hydroxyalkyl group, a $C_3$ or $C_4$ hydroxyalkenyl group, a group —COOR$^3$, —CH$_2$—COOR$^3$, —CH$_2$—CH$_2$—COOR$^3$, or —CH=CH—COOR$^3$, where $R^3$ is a $C_1$-$C_4$ alkyl group, a $C_2$-$C_4$ hydroxyalkyl group, an alkoxyalkyl group with 1 to 4 C atoms in the alkoxy group and 2 to 4 C atoms in the alkyl group or hydrogen or a salt-forming cation, as antiseborrhoeic agents for the preparation of topical, pharmaceutical and cosmetic sebosuppressive preparations.

In the compounds of formula (I), $R^1$ for example may be a cycloaliphatic alkyl group, i.e. an alkyl group containing a cyclopentane, cyclohexane or cycloheptane ring, these cycloalkane rings being optionally substituted by one or more lower alkyl groups. The cycloaliphatic alkyl group is intended to contain a total of about 6 to 20 C atoms. Thus, $R^1$ may be a cyclohexylmethyl group, a 1- or 2-cyclohexylethyl group, a 1-, 2- or 3-cyclohexylpropyl group, a 1-, 2-, 3- or 4-cyclohexylbutyl group, a 4-cyclohexyl-2-butyl group, a 3- or 5-cyclohexylpentyl group, a 6-cyclohexylhexyl group, a 4-(1,1,3-trimethyl-2-cyclohexyl)-2-butyl group, a 4-(3,3,5-trimethylcyclohexyl)-2-butyl group, a 4-(3,3,5-trimethylcyclohexyl)-butyl group, or a 3-(3,3,5-trimethylcyclohexyl)-propyl group.

$R^1$ may also be a mono- or polyunsaturated, cycloaliphatic $C_6$-$C_{20}$ group, for example a 4-cyclohexylbut-3-en-2-yl group, a 4-(1,1,3-trimethyl-2-cyclohexyl)-but-3-en-2-yl group, a 4-(1,1,3-trimethylcyclohex-1-en-2-yl)-but-3-en-2-yl group, a 4-(trimethylcyclohex-1-en-2-yl)-2 butyl group, a 4-(1,1,3-trimethylcyclohex-3-en-2-yl)-2-butyl group or a 4-(3,3,5-trimethyl-1(6)-cyclohexenyl)-2-butyl group.

$R^1$ is preferably a cyclohexylalkyl group or a mono-, di- or trimethylcyclohexylalkyl group containing a total of 6 to 20 C atoms.

Finally, $R^1$ may also be a mono- or polyunsaturated, linear or branched aliphatic $C_6$-$C_{20}$ alkyl group. Groups of this type are, for example, the 11-undecenyl group, the oleyl group, the linoleyl group, the elaidyl group, the linolaidyl group, the arachidyl group and the erucyl group. Preferred unsaturated alkenyl groups are the branched, unsaturated groups derived from terpene alcohols, such as for example the geranyl group, the neryl group, the nerolidyl group, the farnesyl group, the cis- and trans-6,10-dimethyl-5,9-undecadienyl group, the β-citronellyl group, the phytyl group and the isophytyl group.

Where $R^2$ is an ester group, the alcohol radical $R^3$ is, for example, a methyl, ethyl, propyl, isopropyl, butyl, 2-butyl, 2-hydroxyethyl, 2- or 3-hydroxypropyl, 2-methoxyethyl, 2- or 3-methoxypropyl radical.

$R^2$ is preferably a group —CH$_2$OH, —CH=CH—CH$_2$OH, —COOR$^3$, —CH$_2$—CH$_2$—COOR$^3$ or —CH=CH—COOR$^3$, where $R^3$ is preferably hydrogen, a salt-forming cation or a $C_1$-$C_4$ alkyl group.

Some of the alkyl and alkenyl aryl ether derivatives corresponding to general formula (I) are new; as compounds of the basic type known from the publications cited above, they may also be prepared by the general synthesis processes known from the literature which are described in those publications.

The p-alkoxybenzoic acid methyl esters can be prepared, for example, by alkylation of p-hydroxybenzoic acid methyl ester with halides of the formula $R^1$—X (where X is chlorine or bromine for example) or with corresponding sulfates or sulfonic acid esters.

The hydroxyalkyl and alkoxyalkyl esters may then be prepared from the corresponding p-alkoxybenzoic acid methyl esters by transesterification with the particular alcohol components $R^3$—OH in the presence of alkaline catalysts, such as sodium alcoholates for example.

Conversely, esterification of the p-hydroxybenzoic acid may be carried out first, followed by alkylation.

The alkoxycinnamic acid esters, the p-alkoxyphenylpropionic acid esters and the p-alkoxyphenylethanoic acid esters may be prepared analogously to the alkoxybenzoic acid esters from the corresponding p-hydroxyphenylcarboxylic acid methyl esters.

The free acids, in which $R^3$ is hydrogen, may readily be obtained from the corresponding methyl esters by saponification (hydrolysis). They may be converted by neutralization with bases into the salts in which $R^3$ is the salt-forming cation. Particularly suitable, dermatologically compatible salts are the alkali and alkaline earth salts, for example, the sodium, potassium, calcium or magnesium salts and also the ammonium and alkanolammonium salts, for example the monoethanolammonium salt, the isopropanolammonium salt or the triethanolammonium salt. However, salts of other bases are also effective providing they show sufficient dermatological compatibility.

The compounds corresponding to general formula (I), in which $R^2$ is a hydroxyalkyl group, may be prepared by methods known from the literature from the corresponding carboxylic acid methyl esters by reduction with complex metal hydrides, for example with sodium borohydride, lithium aluminum hydride or with sodium-bis-(2-methoxyethoxy)-aluminum hydride (Vitride ®). Examples of the preparation of alkyl or alkenyl aryl ether derivatives of formula (I) that are not known from the literature are given in the Examples.

The alkyl and alkenyl aryl ether derivatives of formula (I) show pronounced sebosuppressive activity, many of the products developing significant sebostatic and antiseborrhoeic effects on the skin in only low in-use concentrations. In addition, they show outstanding compatibility with the skin and mucous membrane. The alkyl and alkenyl aryl ether derivatives corresponding to formula (I) are preferably used in a quantity of 0.0005 to 0.5% by weight in suitable vehicles. They may readily be incorporated in various pharmaceutical and cosmetic vehicles.

Suitable cosmetic vehicles are any preparations suitable for application to the hair or skin. Aqueous or alcoholic solutions, surfactant-containing lotions, oils, ointments, emulsions, creams, gels and stick preparations are particularly suitable for the treatment of skin. Hair lotions, shampoos, hair tonics, hair rinses and hair sprays are particularly suitable for the treatment of hair. On account of the particular cosmetic problems caused by greasy hair, the hair-treatment preparations represent particularly preferred embodiments of the invention.

The most important components of typical cosmetic vehicles are:

(1) oil components, for example paraffin oil, vegetable oils, fatty acid esters, squalene, fatty alcohols, or 2-octyl dodecanol;

(2) fats and waxes, for example spermaceti, beeswax, montan wax, paraffin, or cetostearyl alcohol;

(3) emulsifiers, for example fatty acid partial glycerides, fatty acid sorbitan partial esters and ethoxylates thereof, soaps, fatty alcohol sulfates, fatty alcohol polyglycol ethers, or alkylphosphates;

(4) detergents effective for soil removal during washing, particularly (4.1) anionic surfactants, such as fatty alcohol polyglycol ether sulfates, fatty alcohol sulfates, alpha-olefin sulfonates, alkanesulfonates, sulfosuccinic acid esters, acyl taurides, acyl isothionates, and acyl sarcosines; (4.2) ampholytic surfactants, such as N-alkyl glycine, N-alkylaminopropionic acid, N-alkylaminobutyric acid containing 8 to 18 C atoms in the alkyl group; (4.3) zwitterionic surfactants, such as example N-alkyl-($C_8$-$C_{18}$)-N,N-dimethylammonioglycinate or N-"coconut-acyl"-aminopropyl-N,N-dimethylammonioglycinate, where "coconut-acyl" refers to acyl groups derived from the naturally occurring mixture of long chain carboxy fragments in coconut oil; (4.4) nonionic surfactants, such as fatty alcohol polyglycol ethers, alkylphenol polyglycol ethers, fatty acid polyglycol esters, amine oxide surfactants, fatty acid alkanolamides and ethoxylates thereof; and (4.5) cationic surfactants, such as alkyl ($C_{12}$-$C_{18}$) trimethylammonium chloride, lauryl dimethyl benzylammonium chloride, cetylpyridinium chloride, distearyl dimethylammonium chloride;

(5) lower alcohols, such as ethanol or isopropanol;

(6) polyhydric alcohols, such as ethylene glycol, propylene glycol, or glycerol;

(7) water and auxiliaries, such as perfumes, preservatives, buffers, thickeners, dyes and opacifiers.

Testing and evaluation of the antiseborrhoeic effect

Basis

The test is based on the observation that male rats secrete a brownish sebum so that the degree of greasiness of the skin may readily be visually assessed as browning of the skin. The fact that the browning involves sebum is reflected in the fact that young female rats and male rats washed with surfactant solutions or with lipid solvents, or even male rats systematically treated with estrogen, only show the normal light, pink-colored skin after shearing. At the same time, only very small quantities of lipids can be extracted from the hair cut off; cf. J Soc. Cosmet. Chem. 34, 127–135 (1983)).

Procedure

Male Wistar rats having a body mass of 220 to 230 grams at the beginning of the test were used as the test animals. The test substances, dissolved in a mixtures of equal volumes of ethanol and acetone, were brushed onto half of the back of each of 6 rats for each substance and concentration tested. The other half of the back of each tested rat was treated with the solvent only. One application was made on each tested rat on each of Monday through Friday of one week and on each of Monday through Thursday in the next week; the rats were then evaluated on Friday of the second week. For evaluation, the rats were shaved on their backs and flanks and visually assessed independently by a panel of examiners (6 people) under double-blind conditions. The degree of browning on the backs of the rats was visually assessed as a measure of the sebum coating. A group of six rats of the same type treated on both sides with the solvent only was used for control.

Scoring

The intensities of the brown color on each control rat, and on the side of each other tested rat that had been treated with a solution containing a substance to be tested for its sebosuppressive ability, were scored according to the following scale:

3 points dark brown
2 points mid-brown
1 point light brown
0 point no browning.

The sum of the scores for the six treated rats in each group was divided by the sum of the scores for the six control rats for that group, this quotient was multiplied by 100, and that result subtracted from 100, to give the percentage sebum reduction as recorded in the tables below.

Examples of Practice of the Invention

The following non-limiting examples and comparison examples are intended to illustrate the invention.

1. Preparation Examples

1.1 4-[4-(1,1,3-trimethyl-2-cyclohexyl)-2-butoxy]-benzoic acid methyl ester Methanol was removed by distillation from a mixture of 11.7 g (77 mmol) 4-hydroxybenzoic acid methyl ester, 200 ml N-methylpyrrolidone, and 13.8 g (77 mmol) 30% sodium methylate solution in methanol, then 0.6 g tetrabutylammonium iodide and 20.0 g (92 mmol) 4-(1,1,3-trimethyl-2-cyclohexyl)-2-butyl chloride were added. This was followed by heating with stirring for 8 hours to 160° C. After cooling to room temperature, the reacted solution was filtered off from the sodium chloride formed, concentrated to dryness under reduced pressure, the evaporation residue was taken up in methylene chloride, washed with water, dried with sodium sulfate and, after concentration by evaporation, chromatographed on silica gel (Merck) (eluent: methylene chloride/toluene 7:3). 13.9 g (54% of the theoretical) of 4-(4-(1,1,3-trimethyl-2-cyclohexyl)-butoxy)-benzoic acid methyl ester were obtained in the form of a colorless oil having a refractive index at 20° C. of 1.5197.

1.2 4-cyclohexylmethoxycinnamic acid methyl ester (melting point: 104° C.) was prepared by the method described in 1.1 by substituting, on an equimolar basis, 4-hydroxy-cinnamic acid methyl ester and chloromethyl cyclohexane for the 4-hydroxybenzoic acid methyl ester and 4-(1,1,3-trimethyl-2-cyclohexyl)-2-butyl chloride used in Example 1.1.

1.3 4-(3-cyclohexylpropyloxy)-benzoic acid methyl ester (melting point: 53° to 54° C.) was prepared by the method described in 1.1 by substituting, on an equimolar basis, 4-hydroxy-benzoic acid methyl ester and 3-cyclohexyl-1-chloropropane for the 4-hydroxybenzoic acid methyl ester and 4-(1,1,3-trimethyl-2-cyclohexyl)-2-butyl chloride used in Example 1.1.

Acids were prepared by hydrolysis of portions of the esters prepared in Examples 1.1–1.3 by the following method:

A mixture of 27 mmol of the ester, 20 ml 2-propanol, 15 ml water and 1.3 g sodium hydroxide was heated for 2 hours to the boiling temperature and acidified with concentrated hydrochloric acid to pH 1. After extraction three times by shaking with tert.-butyl methyl ether, washing of the organic phase with water, drying with sodium sulfate and concentration by evaporation, the residue was recrystallized from n-hexane. By this method the following acids were made:

1.4 4-(4-(1,3,3-trimethyl-2-cyclohexyl)-2-butoxy)-benzoic acid from the 4-(4-(1,3,3-trimethyl-2-cyclohexyl)-2-butoxy)-benzoic acid methyl ester made in Example 1.1. 6 g (69% of the theoretical) of colorless 4-(4-(1,1,3-trimethyl-2-cyclohexyl)-2-butoxy)-benzoic acid melting at 114° to 118° C. were obtained.

1.5 4-(cyclohexylmethoxy)-cinnamic acid (melting point: 226° to 228° C.) was prepared from the methyl ester made in Example 1.2.

1.6 4-(3-cyclohexylpropyloxy)-benzoic acid (melting point: 182° to 183° C.) was prepared from the methyl ester made in Example 1.3.

1.7 4-cyclohexylmethoxycinnamic alcohol 7.4 g (36.4 mmol) Vitride ®, which is 70% (sodium-bis-(2-methoxy-ethoxy)-aluminum dihydride), were added dropwise with stirring and cooling with ice at 5° to 15° C. to a solution of 10 g (36.4 mmol) 4-cyclohexyl-methoxycinnamic acid methyl ester (1.2) in 60 ml toluene. The mixture was then heated for 2 hours to the boiling temperature, cooled and 10% sodium hydroxide solution added dropwise thereto while cooling with ice (until the evolution of hydrogen stopped). After addition of approx. 10 ml water and a few drops 2-propanol, the toluene phase was separated off, the aqueous phase was washed twice with toluene, the combined toluene phases were washed with water until neutral and, after drying with sodium sulfate, were concentrated by evaporation. The residue was chromatographed on silica gel (Merck) (eluent: methylene chloride/methanol =99:1). 6.6 g (73% of the theoretical) of 4-cyclohexylmethoxycinnamic alcohol were obtained in the form of a wax-like substance.

1.8 4-farnesyloxybenzoic acid methyl ester

After removal of the methanol by distillation from a mixture of 20.0 g (131 mmol) 4-hydroxybenzoic acid methyl ester, 200 ml N-methylpyrrolidone, and 25.9 g (144 mmol) 30% sodium methylate solution in methanol, 1.1 g tetrabutylammonium iodide and 38.0 g (158 mmol) farnesyl chloride were added. This was followed by heating with stirring for 7 hours at 160° C. After cooling to room temperature, the solution was filtered off from the sodium chloride formed, evaporated under reduced pressure to dryness, the evaporation residue was taken up in methylene chloride, washed with water, dried with sodium sulfate, distilled under reduced pressure after concentration by evaporation and the fraction boiling at 190° to 202° C. under 0.015 mbar pressure was chromatographed on silica gel (Merck) (eluent: methylene chloride/toluene =7:3). 19.2 g (41% of the theoretical) of 4-farnesyloxybenzoic acid methyl ester was obtained in the form of a colorless oil having a refractive index at 20° C. of 1.5293.

1.9 4-geranyloxybenzoic acid methyl ester ($n^{20}$ :1.5300; melting point: 30° to 33° C.) was prepared by the method described in Example 1.8, substituting on an equimolar basis geranyl chloride for the farnesyl chloride used in Example 1.8.

1.10 4-phytyloxybenzoic acid methyl ester ($n^{20}$: 1.4995) was prepared by the method described in 1.8, substituting on an equimolar basis phytyl chloride for the farnesyl chloride used in Example 1.8.

1.11 3-(4-farnesyloxyphenyl)-propionic acid methyl ester ($n^{20}$: 1.5162) was prepared by the method described in 1.8, substituting on an equimolar basis 3-(4-hydroxyphenyl)-propionic acid methyl ester for the 4-hydroxybenzoic acid methyl ester used in Example 1.8.

1.12 4-farnesyloxycinnamic acid methyl ester ($n^{20}$: 1.5571) was prepared by the method described in 1.8, substituting on an equimolar basis 4-hydroxycinnamic acid methyl ester for the 4-hydroxybenzoic acid methyl ester used in Example 1.8.

Samples of the esters made in Examples 1.10–1.12 were hydrolyzed to produce acids by the same procedure as already described above for hydrolyzing the esters made in Examples 1.1–1.3. By this means were made:

1.13 3-(4-farnesyloxyphenyl)-propionic acid (in 75% of the theoretical yield)

a light yellow, viscous oil having a refractive index $n^{20}$ of 1.5041.

1.14 4-farnesyloxycinnamic acid (melting point: 70° to 73° C.)

1.15 4-phytyloxybenzoic acid (thick highly viscous mass)

1.16 4-farnesyloxybenzoic acid (melting point: 63° to 71° C.)

1.17 4-farnesyloxybenzyl alcohol 4 g (14 mmol) Vitride ®, which is 70% sodium bis-(2-methoxy-ethoxy)-aluminum dihydride, were added dropwise with stirring and cooling with ice at 5° to 15° C. to a solution of 5 g (14 mmol) 4-farnesyloxybenzoic acid methyl ester in 30 ml toluene. The mixture was then heated for 2 hours to the boiling temperature, cooled and 10% sodium hydroxide solution added dropwise while cooling with ice (until the evolution of hydrogen stopped). After approx. 10 ml water and a few drops 2-propanol had been added, the toluene phase was separated off, the aqueous phase was washed twice with toluene and, after drying with sodium sulfate, was concentrated by evaporation. The residue was chromatographed on silica gel (Merck) (eluent: methylene chloride/methanol 99:1). 4-farnesyloxybenzyl alcohol having a refractive index $n^{20}$ of 1.5305 was obtained in a yield of 3.6 g (78% of the theoretical).

The percentage sebum reduction, measured by the method described above, obtained with the compounds prepared in Examples 1.1 to 1.17 are shown in Table 1.

TABLE I

| Product of Example No. | Concentration % by Weight | Percentage Sebum Reduction |
| --- | --- | --- |
| 1.1 | 0.01 | 25 |
| 1.1 | 0.05 | 99 |
| 1.2 | 0.5 | 29 |
| 1.3 | 0.02 | 0 |
| 1.3 | 0.05 | 68 |
| 1.3 | 0.5 | 99 |
| 1.4 | 0.001 | 73 |
| 1.4 | 0.005 | 88 |
| 1.4 | 0.01 | 93 |
| 1.4 | 0.05 | 100 |
| 1.5 | 0.5 | 15 |
| 1.6 | 0.005 | 0 |
| 1.6 | 0.01 | 52 |
| 1.6 | 0.02 | 84 |
| 1.7 | 0.1 | 53 |
| 1.7 | 0.5 | 66 |
| 1.8 | 0.01 | 38 |
| 1.8 | 0.05 | 86 |
| 1.9 | 0.1 | 40 |
| 1.11 | 0.05 | 86 |

TABLE I-continued

| Product of Example No. | Concentration % by Weight | Percentage Sebum Reduction |
| --- | --- | --- |
| 1.12 | 0.05 | 85 |
| 1.13 | 0.05 | 68 |
| 1.14 | 0.05 | 73 |
| 1.15 | 0.05 | 35 |
| 1.16 | 0.01 | 69 |
| 1.17 | 0.001 | 14 |
| 1.17 | 0.002 | 18 |
| 1.17 | 0.005 | 72 |
| 1.17 | 0.01 | 87 |
| 1.17 | 0.05 | 86 |

3. Examples of Preparations According to the Invention

3.1 Shampoo for greasy hair

| | |
| --- | --- |
| Texapon ® N 25 (1) | 40% by weight |
| Comperlan ® KD (2) | 3 |
| Product of Example 1.4 | 0.1 |
| Bronidox ® L (3) | 0.2 |
| Water | Balance |

3.2 Fast-acting hair tonic emulsion

| | |
| --- | --- |
| Cetyl alcohol | 3.0% by weight |
| Dehyquart ® A (4) | 2.0 |
| Product of Example 1.6 | 0.02 |
| Citric acid | 1.0 |
| Water | Balance |

3.3 Fast-acting hair tonic, clear

| | |
| --- | --- |
| Cetiol ® HE (5) | 20.0% by weight |
| Cetylpyridinium chloride | 5.0 |
| Glycerol | 5.0 |
| Product of Example 1.8 | 0.05 |
| Isopropanol | Balance |

3.4 Hair lotion

| | |
| --- | --- |
| Cetiol ® HE (5) | 2.0% by weight |
| Birch extract | 1.0 |
| Product of Example 1.17 | 0.005 |
| Isopropanol | 30.0 |
| Water | Balance |

3.5 Skin emulsion, oil in water

| | |
| --- | --- |
| Cutina ® MD (6) | 7.0% by weight |
| Eumulgin ® B1 (7) | 3.0 |
| Cetiol ® SN (8) | 10.0 |
| Myritol ® 318 (9) | 10.0 |
| Product of Example 1.4 | .01 |
| Water | Balance |

3.6 Skin cream, oil in water

| | |
| --- | --- |
| Cutina ® MD (6) | 17% by weight |
| Eumulgin ® B1 (7) | 3 |
| Eutanol ® G (10) | 11 |
| Myritol ® 318 (9) | 6 |
| Carrot oil CLR | 3 |
| Product of Example 1.1 | 0.02 |
| Water | ad 100 |

The trade names used in the Formulation Examples have the following meanings:
(1) Texapon ® N 25: 28% aqueous solution of alkyl($C_{12}$–$C_{14}$) poly(2 EO)glycol ether sulfate, Na salt (Henkel KGaA)
(2) Comperlan ® KD: coconut oil fatty acid diethanolamide (Henkel KGaA)
(3) Bronidox ® L: 5-bromo-5-nitro-1,3-dioxane (10% solution in 1,2-propylene glycol) (Henkel KGaA)
(4) Dehyquart ® A: cetyl trimethylammonium chloride (25% solution in water) (Henkel KGaA)
(5) Cetiol ® HE: polyol fatty acid ester (CTFA name: PEG-7-Glyceryl-Cocoate) (Henkel KGaA)
(6) Cutina ® MD: palmitic/stearic acid mono/diglyceride (Henkel KGaA)
(7) Eumulgin ® B1: cetostearyl alcohol + 12 mol ethylene oxide (Henkel KGaA)
(8) Cetiol ® SN: cetostearyl isononanoate (Henkel KGaA)
(9) Myritol ® 318: caprylic/capric acid triglyceride (Henkel KGaA)
(10) Eutanol ® G: 2-octyldodecanol (Henkel KGaA)

We claim:

1. A preparation suitable for topical application to human skin, comprising a sebosuppressive effective amount of a compound corresponding to the formula:

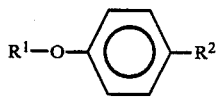 (I)

in which
(a) $R^1$ is a monovalent saturated hydrocarbon group containing at least one cyclopentane, cyclohexane, or cycloheptane ring nucleus and a total of about 6–20 carbon atoms; or a mono- or polyunsaturated, linear, branched, or cycloaliphatic group having about 6–20 carbon atoms;
(b) $R^2$ is selected from the group consisting of about $C_1$–$C_4$ hydroxy-alkyl, about $C_3$ or $C_4$ hydroxyalkenyl, —COOR$^3$, —CH$_2$—COOR$^3$, —CH$_2$—CH$_2$—COOR$^3$, and —CH=CH—COOR$^3$,
wherein $R^3$ is an about $C_1$–$C_4$ alkyl group, an about $C_2$–$C_4$ hydroxyalkyl group, an alkoxyalkyl group with about 1 to 4 carbon atoms in the alkoxy group and about 2 to 4 carbon atoms in the alkyl group, hydrogen, or a salt-forming cation and a topical vehicle therefore.

2. A preparation according to claim 1, wherein $R^1$ contains a cyclohexyl nucleus, and $R^2$ is a group, —CH$_2$OH, —CH=CH—CH$_2$OH, —COOR$^3$, —CH$_2$—CH$_2$—COOR$^3$ or —CH=CH—COOR$^3$, where $R^3$ is hydrogen, a salt-forming cation, or an about $C_1$–$C_4$ alkyl group.

3. A preparation according to claim 1, wherein $R^1$ is a group derived from unsaturated terpene alcohols by removal of one hydroxyl group therefrom.

4. A preparation according to claim 3, wherein $R^1$ is a geranyl, neryl, nerolidyl, farnesyl, 6,10-dimethyl-5,9-undecadienyl, β-citronellyl, phytyl or isophytyl group.

5. A preparation according to claim 4, wherein the amount of sebosuppressive compound is about 0.0005 to about 0.5 weight percent of the preparation as a whole.

6. A preparation according to claim 3, wherein the amount of sebosuppressive compound is about 0.0005 to about 0.5 weight percent of the preparation as a whole.

7. A preparation according to claim 2, wherein the amount of sebosuppressive compound is about 0.0005 to about 0.5 weight percent of the preparation as a whole.

8. A preparation according to claim 1, wherein the amount of sebosuppressive compound is about 0.0005 to about 0.5 weight percent of the preparation as a whole.

9. A method for treating human skin or hair, comprising applying thereto a subsuppressive amount of a preparation according to claim 8.

10. A method for treating human skin or hair, comprising applying thereto a preparation according to claim 7.

11. A method for treating human skin or hair, comprising applying thereto a preparation according to claim 6.

12. A method for treating human skin or hair, comprising applying thereto a preparation according to claim 5.

13. A method for treating human skin or hair, comprising applying thereto a preparation according to claim 4.

14. A method for treating human skin or hair, comprising applying thereto a preparation according to claim 3.

15. A method for treating human skin or hair, comprising applying thereto a preparation according to claim 2.

16. A method for treating human skin or hair, comprising applying thereto a preparation according to claim 1.

* * * * *